(12) United States Patent
Bonrath et al.

(10) Patent No.: US 8,592,636 B2
(45) Date of Patent: Nov. 26, 2013

(54) HYDROGENATION PROCESS

(75) Inventors: Werner Bonrath, Basel (CH); Thomas Mueller, Basel (CH); Lioubov Kiwi-Minsker, St. Sulpice (CH); Albert Renken, St. Sulpice (CH); Igor Iouranov, Chavannes (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/575,096

(22) PCT Filed: Jan. 28, 2011

(86) PCT No.: PCT/EP2011/051197
§ 371 (c)(1),
(2), (4) Date: Jul. 25, 2012

(87) PCT Pub. No.: WO2011/092280
PCT Pub. Date: Aug. 4, 2011

(65) Prior Publication Data
US 2012/0302801 A1 Nov. 29, 2012

(30) Foreign Application Priority Data
Jan. 28, 2010 (EP) .................................... 10000862

(51) Int. Cl.
*C07C 29/17* (2006.01)
(52) U.S. Cl.
USPC .................... 568/903; 568/803; 568/909.5
(58) Field of Classification Search
USPC ........................................ 568/903, 909.5
See application file for complete search history.

(56) References Cited

FOREIGN PATENT DOCUMENTS

WO WO 2008/101603 8/2008

OTHER PUBLICATIONS

International Search Report for PCT/EP2011/051197, mailed Jul. 5, 2011.
Semagiana et al., "Structured catalyst of pd//ZnO on sintered metal fibers for 2-methyl-3-butyn-2-ol selective hydrogenation", Journal of Catalysis, vol. 251, No. 1, (Sep. 7, 2007), pp. 213-222.
Semagina, N. et al., "Palladium Nanohexagons and Nanospheres in Selective Alkyne Hydrogenation", Catalysis Letters, vol. 127, No. 3-4, (Oct. 11, 2008), pp. 334-338.
Ferreira, F. et al., "Expeditous Synthesis of a Common Intermediate of L-1-Deoxyallonojirimycin and L-1-Deoxymannojirimycin", Journal of Organic Chemistry, vol. 74, (2009), pp. 2238-2241.
Rylander, *"Catalytic Hydrogenation over Platinum Metals"*, Academic Press, pp. 74-79 (1967).
Mäeorg et al, *"New Activated Zn—Cu-catalyst—Superior Tool for the Partial Hydrogenation of Triple Bonds"*, Tartu University, May 29, 2013, www.ch.ic.ac.uk/ectoc/papers/14/.
Murillo et al, *"The effect of hydrocarbon structure and chain length on the low-temperature hydrogenation activity on Ni/Pt(111) bimetallic surfaces"*, Surface Science 594 (2005) 27-42.

*Primary Examiner* — Elvis O Price
(74) *Attorney, Agent, or Firm* — Nixon & Vanderhye P.C.

(57) ABSTRACT

The present invention relates to a process of reacting specific compounds, which are defined below with hydrogen in the presence of a structured catalyst based on sintered metal fibers (SMF) coated by a ZnO layer with Pd-nanoparticles, to reactions of these specific compounds with hydrogen in the presence of said catalyst and an organic base as well as to vitamins, carotinoids, perfume ingredients, and/or food or feed ingredients prepared by using this reaction.

45 Claims, No Drawings

HYDROGENATION PROCESS

This application is the U.S. national phase of International Application No. PCT/EP2011/051197, filed 28 Jan. 2011, which designated the U.S. and claims priority to EP Application No. 10000862.2, filed 28 Jan. 2010, the entire contents of each of which are hereby incorporated by reference.

The present invention relates to a process of reacting specific compounds, which are defined below, with hydrogen in the presence of a structured catalyst based on sintered metal fibers (SMF) coated by a ZnO layer with Pd-nanoparticles, to reactions of these specific compounds with hydrogen in the presence of said catalyst and an organic base as well as to vitamins, carotinoids, perfume ingredients, and/or food or feed ingredients prepared by using this reaction.

Selective catalytic hydrogenations of alkynols to alkenols are important processes in the fine chemicals industry. Pd-based catalysts are known to give the highest selectivity and yield. Preferential formation of olefinic alcohols is attributed to the stronger adsorption of acetylenic alcohols in comparison with the half-hydrogenation product. Catalytic performance of palladium is known to be strongly influenced by its dispersion, nature of support and the use of promoters and additives. Catalyst design taking into consideration these factors can allow a yield increase of target product and catalyst reuse.

In general, Pd atoms of low coordination number present in small particles of 1 to 2 nm provide too strong alkynol adsorption diminishing turnover frequency and selectivity. This phenomenon is known as a geometric or "ensemble" effect. Particles of 7 to 10 nm size demonstrate better catalytic performance in hydrogenations of 2-butyne-1,4-diol and 2-methyl-3-butyn-2-ol (MBY) as compared to highly dispersed Pd.

In industry hydrogenations as describes above are usually carried out in stirred tank reactors with Lindlar catalyst, 5% Pd/CaCO$_3$ modified by lead acetate and often with addition of quinoline. Lindlar catalyst being a fine powder is difficult to handle and requires filtration after the reaction. In this respect, structured catalysts are beneficial for process intensification and safety. Monoliths, membranes, metallic grids, bidimensional glass and carbon were used as catalyst supports in liquid-phase hydrogenations. Monoliths showed similar selectivity but much lower activity per Pd loading in comparison with a slurry catalyst in 3-methyl-1-pentyn-3-ol and 2-butyne-1,4-diol hydrogenations. The use of highly-selective bimetallic Pd—Ru (9:1) H$_2$-permeable membrane in 2-methyl-3-butyn-2-ol hydrogenation is limited by the high content of noble metal and low productivity per gram of Pd. Metallic grids have a disadvantage of low geometric surface area of ~100 cm$^2$/g. Fabrics of activated carbon fibers used in 2-butyne-1,4-diol hydrogenation possess low mechanical strength. Therefore, there is a need for a hydrogenation process which may overcome the above-mentioned disadvantages.

It was surprisingly found that the combination of a structured catalyst with an organic base (preferably comprising at least one nitrogen atom, sulphur atom and/or phosphor atom, more preferably comprising at least one sulphur atom) allows a good and very selective hydrogenation of compounds of formula (I) as defined below.

Therefore, the present invention relates to a process of reacting a compound of formula (I)

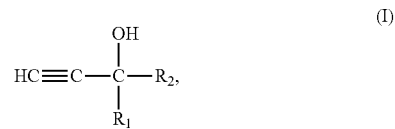

wherein
R$_1$ is linear or branched C$_5$-C$_{35}$ alkyl or linear or branched C$_5$-C$_{35}$ alkenyl moiety, wherein the C chain can be substituted, and
R$_2$ is linear or branched C$_1$-C$_4$ alkyl, wherein the C chain can be substituted, with hydrogen in the presence of
(i) a structured catalyst based on sintered metal fibers (SMF) coated by a ZnO layer with Pd-nanoparticles and
(ii) at least one organic base.

The hydrogenated forms of compounds of formula (I) can be used as intermediates in the synthesis of important compounds such as vitamins A and E and perfumes. Three-dimensional sintered metal fibers (SMF) consisting of metallic microfibers were chosen as a structured catalyst support. SMF have high thermal conductivity that is a great advantage in exothermic hydrogenations, high porosity and permeability. The metal fiber matrix also acts as a micron-scale static mixer eliminating channeling. In addition, high mechanical strength, chemical and thermal stability, easy shaping make SMF promising materials for intensification of catalytic hydrogenation.

SMF were coated with a thin layer of ZnO known as efficient support for 2-methyl-3-butyn-2-ol hydrogenation. Pd nanoparticles were deposited from the beforehand prepared sol, and the material was heated in hydrogen atmosphere to create Pd$_y$Zn$_x$ phase. ZnO layer acts both as a basic support and a Pd promoter. The Pd/ZnO/SMF material was tested for mechanical stability, and its catalytic behavior was studied in MBY hydrogenation.

The term "structured catalyst" as used herein refers to catalysts wherein the spatial position of the catalyst is controlled. Structured catalysts are known in the art, see, e.g., *Chimia* 56(4), 2002, 159-163. Examples of structured catalysts are ceramic carrier constructions and fibrous structures, especially filamentous (woven or not) materials. All types of filamentous materials can be used in the present invention. The fibers may be from organic or inorganic matter. Examples are: fabrics from activated carbon fibers, glass fibers, ceramic fibers, composite oxides fibers, and metal fibers filters or fleece. Preferred are metal fiber materials. The individual fibers of these materials preferably have a diameter of about 2 μm to about 100 μm, especially a diameter of no more than about 20 μm. The materials may be chemically treated, to modify the specific surface area and/or may have a coating, e.g. of metal oxides such as Al, Ti, Mg, Zn, etc.

In a preferred embodiment of the present invention the SMF consist of a FeCrAl alloy, which optionally can be pre-oxidised.

In a further embodiment of the present invention the Pd-nanoparticles are Pd$^0$-nanoparticles.

A further embodiment of the present invention relates to a process, wherein a portion of the Pd-nanoparticles are within Pd$_y$Zn phase, which is preferably formed through thermal activation in a hydrogen atmosphere.

Usually the Pd-nanoparticles have a size between 0.5 and 20 nm, preferably between 2 and 15 nm, more preferably between 5 and 12 nm and most preferably between 7 to 10 nm.

The present invention further relates to a process as defined above, wherein the catalyst is containing between 0.001 and 5 weight-% (wt-%) of Pd nanoparticles, preferably between 0.01 and 2 wt-% more preferably between 0.05 and 1 wt-% and most preferably between 0.1 and 0.3 and wt-%, based on the total weight of the catalyst. The catalyst can also comprise further metals.

Therefore a further embodiment of the present invention relates to a process as defined above, wherein the catalyst comprises further a co-metal selected from the group consisting of Pb, Mn, Cu, Bi, Sn, Au, Ag, Zn and Cd.

In a preferred embodiment the ZnO layer is a grain-structured ZnO layer.

Usually the catalyst used in the process according to the present invention is comprising between 0.01 and 20 wt-% of ZnO, preferably between 0.1 and 10 wt-% more preferably between 1.5 and 10 wt-% and most preferably between 2 and 8-wt-%, based on the weight of the catalyst.

Compounds of formula (I)

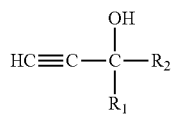

wherein the substituents are defined as disclosed above, are used in the process according to this invention.

In a preferred embodiment of the present invention compounds of formula (I), wherein $R_1$ is a linear or branched $C_5$-$C_{30}$ alkyl moiety or a linear or branched $C_5$-$C_{30}$ alkenyl moiety, wherein the C chain can be substituted, and $R_2$ is a linear or branched $C_1$-$C_4$ alkyl moiety, wherein the C chain can be substituted, are used.

In a more preferred embodiment of the present invention compounds of formula (I), wherein $R_1$ is a linear or branched $C_6$-$C_{16}$ alkyl moiety or a linear or branched $C_6$-$C_{16}$ alkenyl moiety, wherein the C chain can be substituted, and $R_2$ is a $C_1$-$C_2$ alkyl moiety, wherein the C chain can be substituted.

In a most preferred embodiment of the present invention compounds of formula (I), wherein $R_1$ is a linear or branched $C_6$-, $C_{11}$- or $C_{16}$-alkyl moiety or a linear or branched $C_6$-, $C_{11}$- or $C_{16}$-alkenyl moiety, and $R_2$ is a $C_1$-$C_2$ alkyl moiety.

An organic base is used in the process according to the present invention. The organic base comprises at least one nitrogen atom, sulphur atom and/or phosphor atom.

Preferably the organic base comprises at least one nitrogen atom or at least one sulphur atom, more preferably at least one sulphur atom.

More preferably the organic base is chosen from the group consisting of 3,6-dithia-1,8-octandiol, thiophene, dipropyl sulfide, tetrahydrothiophene, quinoline, pyridine and diethylaminoethanol.

Usually a process according to the present invention comprises an "organic base-to-Pd molar ratio" from 1 to 1500.

The hydrogenation in accordance with the present invention can be carried out under conditions conventionally used for hydrogenations. Suitably, the hydrogenation is carried out at a pressure of about 0.1 to about 6 MPa and at a temperature of about 350 K to about 500 K. The hydrogenation can be carried out batch wise or in continuous mode.

The following Example illustrates the invention further without limiting it. All percentages and parts, which are given, are related to the weight and the temperatures are given in K or in ° C., when not otherwise stated.

EXAMPLES

Materials

SMF (from Southwest Screens & Filters SA, Belgium) made of FeCrAl alloy fibers (Cr 20%, A14.75%, Y 0.27%, other elements ~1-2%, Fe balance) in the form of a uniform pore panel (0.29 mm thickness, 71% porosity, 20μ fiber thickness, 675 g/m²) are used as a structured support.

Preparation of Pd/ZnO/SMF Catalyst (0.2 wt-% Pd {3 wt-% to ZnO}, 6 wt-% ZnO)

In order to remove contaminations the SMF panels are degreased with acetone, boiled in toluene for 0.5 h and air-dried. To improve further the adhesion of ZnO, SMF are oxidized in air at 1373 K for 3 h to create an α-Al₂O₃ surface layer. Such a temperature (1373-1473 K) for the treatment of FeCrAl alloy with little rare earth content is known to lead to the formation of a structured alumina film, characterized by equiaxed grains on the outer surface, while lower temperature treatment gives oxide whiskers.

The ZnO film is prepared by sol-gel method using zinc acetate dihydrate (0.3 M in isopropanol) and solubility enhancement additives (monoethanolamine MEA and acetoin AlN) at a molar ratio of MEA:AlN:Zn=1:0.5:1. The additives are mixed in a solvent prior to the addition of zinc acetate with the help of ultrasound, the sol is colored reddish brown due to reaction between MEA and AlN yielding imine HO—CH(CH₃)—C(CH₃)=N—C₂H₄—OH. Coating is conducted by a dip-coating procedure. The gel film thus obtained is air-dried at 383 K for 10 min and then heated at 873 K for 30 min. Rapid heating is applied which is known to result in the formation of highly oriented crystals (slow heating, on the other hand, gives complicated structures). The coating-heating procedure is repeated 7 times to give the weight gain of 6 wt-% ZnO. The coating then is post-annealed at 1173 K for 15 min to promote the formation of island structure of ZnO grains with the increased the specific surface area.

Pd sol is prepared as described in via dissolution of PdCl₂ in a boiling aqueous solution of sodium molybdate at a molar ratio Mo:Pd=1.2, followed by hydrogenation for 30 min at room temperature. After wet impregnation for 1 hour, ZnO/SMF panels are washed copiously with water, dried at ambient conditions and subjected to high-temperature treatment in hydrogen atmosphere (H₂:Ar=1:9, total flow of 450 mL/mn, 2 h at room temperature, 10°/min to 573 K, hold for 2 hours and cooled at the same flow). Catalyst is stored at ambient conditions. Such a process is described in WO 2008/101603.

2.3. Catalysts Characterization

The Pd and Zn amounts after dissolution in hot nitric acid are determined by atomic absorption spectroscopy via Shimadzu AA-6650 spectrometer with an airacetylene flame. The ZnO loading is also determined gravimetrically.

The BET specific surface area and pores size distribution (PSD) of the support and the catalyst are determined using a Sorptomatic 1990 (Carlo Erba) instrument via N₂ adsorption-desorption at 77 K. PSD calculation is performed by Dollimore/Heal method.

The ultrasonic adherence test for the mechanical stability of the catalyst is carried out using an ultrasonic bath (Bransonic ultrasonic cleaner, Branson Ultrasonic Corp., USA). The catalyst is treated in water for 20 min totally, and after each 5 min the material is dried at 393 K and weighed.

The surface morphology of the samples is investigated by scanning electron microscopy SEM, using a JSM-6300F, JEOL. XRD analysis is carried out in a Siemens D 500 diffractometer using $CuK_\alpha$ radiation. The spectra are recorded in a rapid scanning mode (4.0 s/step, 2θ step size of 0.04°) in a 2θ range of 30 to 50°.

Continuous Hydrogenation of Dehydroisophytol (DIP) to Isophytol (IP)

In a 500 ml stainless steel autoclave, equipped with a stirrer, temperature- and pressure-control, about 1.8 g catalyst (0.2 g Pd on ZnO on FeCrAl-alloy) and a mixture of 233.1 g DIP/IP (1/4) was added. The reactor is heated under hydrogen pressure to 85° C. and 4 bar (absolute pressure) and the reaction mixture is stirred (with 1250 rpm). The reaction is carried out by feeding of DIP and a constant level is controlled inside the reactor. The organic base (3,6-dithia-1,8-octandiol) is added with the feed-stream during the hydrogenation reaction. The reaction is performed at 80% conversion. Sampling during the reaction and analyzing by GC indicates the ongoing reaction. At the end, the crude reaction product is collected and analyzed.

TABLE 1

|  | Example 1 (comparison test) | Example 2 |
|---|---|---|
| Catalyst | 0.2% Pd/5.1% ZnO on Fe—CrAlloy-, 40 μm | 0.2% Pd/5.1% ZnO on FeCrAlloy, 40 μm |
| Amount catalyst | 1.74 g | 1.76 g |
| Organic base | — | 3,6-Dithia-1,8-octandiol |
| Reaction time (h) | 810 | 1480 |
| Temperature (T) | 85° C. | 85° C. |
| Pressure | 4 bara | 4 bara |
| amount Organic base | — | 0.08 mg/g catalyst |
| Conversion (%) | 80% | 80% |
| Selectivity (%) | 80% | 93% |
| Yield (%) | 64% | 73% |

The selectivity of the process according to the present invention is significantly higher than the one of the prior art.

Hydrogenation of Dehydroisophytol (DIP) to Isophytol (IP)

Solvent-free selective hydrogenation of dehydroisophytol (DIP) to isophytol (IP) was carried out in a 250 ml reactor at 80° C. under $H_2$ pressure (4 bar) using 200 ml of DIP and the catalysts (0.8 to 0.9 g) prepared as described above. At the end, the crude reaction product is collected and analyzed.

TABLE 2

|  | Example 3 | Example 4 | Example 5 |
|---|---|---|---|
| Catalyst | 0.2% Pd/5.1% ZnO on FeCrAlloy, 40 μm | 0.2% Pd/5.1% ZnO on FeCrAlloy, 40 μm | 0.2% Pd/5.1% ZnO on FeCrAlloy, 40 μm |
| Amount catalyst | 0.89 g | 0.89 g | 0.89 g |
| Organic base | 3,6-Dithia-1,8-octandiol | 3,6-Dithia-1,8-octandiol | 3,6-Dithia-1,8-octandiol |
| Reaction time (h) | 2 | 3.5 | 4.5 |
| Temperature (T) | 80° C. | 80° C. | 80° C. |
| Pressure | 4 bara | 4 bara | 4 bara |
| amount Organic base | 0.006 mg/g catalyst | 0.02 mg/g catalyst | 0.05 mg/g catalyst |
| Conversion (%) | 98% | 98% | 98% |
| Selectivity (%) | 91.4% | 94.2% | 95.6% |
| Yield (%) | 89.5% | 92.3% | 93.7% |

Continuous Hydrogenation of Dehydroisophytol (DIP) to Isophytol (IP)

Example 6

In a 500 ml stainless steel autoclave, equipped with a stirrer, temperature- and pressure-control, 1.7 g catalyst (0.2 g Pd on ZnO on FeCrAl-alloy) are placed a mixture of 233.1 g DIP/IP (1/4). The reactor is heated under hydrogen pressure to 90° C. and 4 bar (absolute pressure) and the reaction mixture is stirred (with 1250 rpm). The reaction is carried out by feeding of DIP and a constant level is controlled inside the reactor. The organic base (3,6-dithia-1,8-octandiol) is added with the feed-stream during the hydrogenation reaction. The reaction is performed at 80% conversion. Sampling during the reaction and analyzing by GC indicates the ongoing reaction. At the end, the crude reaction product is collected and analyzed.

| Catalyst | 0.2% Pd/5.1% ZnO on FeCrAlloy, 40 μm |
|---|---|
| Amount catalyst | 1.76 g |
| Organic base | 3,6-Dithia-1,8-octandiol |
| Reaction time (h) | 72 |
| Temperature (T) | 90° C. |
| Pressure | 4 bara |
| Range Organic baser | 0.08 mg/g catalyst |
| Conversion (%) | 80% |
| Selectivity (%) | 92% |
| Yield (%) | 73.6% |

Example 7

The experiment has been done in accordance to Example 2, except that a lower temperature (75° C.) has been used.

| Catalyst | 0.2% Pd/5.1% ZnO on FeCrAlloy, 40 μm |
|---|---|
| Amount catalyst | 1.76 g |
| Organic base | 3,6-Dithia-1,8-octandiol |
| Reaction time (h) | 72 |
| Temperature (T) | 75° C. |
| Pressure | 4 bara |
| amount Organic base | 0.08 mg/g catalyst |
| Conversion (%) | 80% |
| Selectivity (%) | 92.5% |
| Yield (%) | 73.6% |

The invention claimed is:

1. A hydrogenation process which comprises reacting a compound of formula (I)

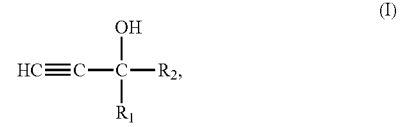

with hydrogen in the presence of:
(i) a structured catalyst based on sintered metal fibers (SMF) coated by a ZnO layer impregnated with Pd-nanoparticles, and
(ii) at least one organic base, wherein $R_1$ is a linear or branched $C_5$-$C_{35}$ alkyl moiety or a linear or branched $C_5$-$C_{35}$ alkenyl moiety, wherein the C chain can be substituted, and $R_2$ is a linear or branched $C_1$-$C_4$ alkyl moiety, wherein the C chain can be substituted.

2. The process according to claim 1, wherein the SMF comprises FeCrAl alloy.

3. The process according to claim 1, wherein the Pd-nanoparticles are $Pd^0$-nanoparticles.

4. The process according to claim 1, wherein a portion of the Pd-nanoparticles is in a $Pd_yZn$ phase.

5. The process according to claim 1, wherein the Pd-nanoparticles have a size of between 0.5 and 20 nm.

6. The process according to claim 1, wherein the catalyst contains between 0.001 and 5 wt-% Pd nanoparticles, based on the total weight of the catalyst.

7. The process according to claim 1, wherein the catalyst comprises a co-metal selected from the group consisting of Pb, Mn, Cu, Bi, Sn, Au, Ag, Zn and Cd.

8. The process according to claim 1, wherein the ZnO layer is a grain-structured ZnO layer.

9. The process according to claim 1, wherein the catalyst comprises between 0.01 and 20 wt-% of ZnO, based on the weight of the catalyst.

10. The process according to claim 1, wherein
$R_1$ is a linear or branched $C_5$-$C_{30}$ alkyl moiety or a linear or branched $C_5$-$C_{30}$ alkenyl moiety, wherein the C chain can be substituted, and
$R_2$ is a linear or branched $C_1$-$C_4$ alkyl moiety, wherein the C chain can be substituted.

11. The process according to claim 1, wherein
$R_1$ is a linear or branched $C_6$-$C_{16}$ alkyl moiety or a linear or branched $C_6$-$C_{16}$ alkenyl moiety, wherein the C chain can be substituted, and
$R_2$ is a $C_1$-$C_2$ alkyl moiety, wherein the C chain can be substituted.

12. The process according to claim 1, wherein
$R_1$ is a linear or branched $C_6$-, $C_{11}$- or $C_{16}$- alkyl moiety or a linear or branched $C_6$-, $C_{11}$- or $C_{16}$- alkenyl moiety, and
$R_2$ is a $C_1$-$C_2$ alkyl moiety.

13. The process according to claim 1, wherein the organic base comprises at least one nitrogen atom, sulphur atom and/or phosphor atom.

14. The process according to claim 13, wherein the organic base comprises at least one nitrogen atom and/or at least one sulphur atom.

15. The process according to claim 13, wherein the organic base is chosen from the group consisting of 3,6-dithia-1,8-octandiol, thiophene, dipropyl sulfide, tetrahydrothiophene, quinoline, pyridine and diethylaminoethanol.

16. The process according to claim 1, which comprises using a molar ratio of the organic base-to-Pd of 1 to 1500.

17. The process according to claim 1, wherein the process is practiced at a pressure between 1.1 and 30 bars.

18. The process according to claim 1, wherein the process is practiced at a reaction temperature between 250 K and 400 K.

19. The process according to claim 1, further comprising adding quinoline to the reaction.

20. The process according to claim 19, wherein the quinolone is added at a ratio of the quinoline to the Pd of between 1:1 and 500:1.

21. The process according to claim 1, wherein the process is carried out in a solvent.

22. The process according to claim 21, wherein the solvent is water.

23. The process according to claim 1, wherein the process further comprises separating used SMF after the reaction and exposing the used SMF to ultrasonic radiation.

24. The process according to claim 1, wherein the reaction product is an Intermediate of a vitamin, a carotinoid, a perfume ingredient, and/or a food ingredient.

25. The process according to claim 23, which comprises exposing the used SMF to ultrasonic radiation in a vessel containing ethanol or iso-propanol.

26. The process according to claim 2, wherein the FeCrAl alloy is preoxidized.

27. The process according to claim 4, wherein $Pd_yZn$ phase is formed through thermal activation in a hydrogen atmosphere.

28. The process according to claim 5, wherein the Pd-nanoparticles have a size of between 2 and 15 nm.

29. The process according to claim 5, wherein the Pd-nanoparticles have a size of between 5 to 12 nm.

30. The process according to claim 5, wherein the Pd-nanoparticles have a size of between 7 to 10 nm.

31. The process according to claim 6, wherein the catalyst contains between 0.01 and 2 wt-% of Pd nanoparticles, based on the total weight of the catalyst.

32. The process according to claim 6, wherein the catalyst contains between 0.05 and 1 wt-% of Pd nanoparticles, based on the total weight of the catalyst.

33. The process according to claim 6, wherein the catalyst contains between 0.1 and 0.3 wt-% of Pd nanoparticles, based on the total weight of the catalyst.

34. The process according to claim 9, wherein the catalyst comprises between 0.1 and 10 wt-% of ZnO, based on the weight of the catalyst.

35. The process according to claim 9, wherein the catalyst comprises between 1.5 and 10 wt-% of ZnO, based on the weight of the catalyst.

36. The process according to claim 9, wherein the catalyst comprises between 2 and 8 wt-% of ZnO, based on the weight of the catalyst.

37. The process according to claim 17, wherein the pressure is between 1.1 and 15 bars.

38. The process according to claim 17, wherein the pressure is between 1.5 and 10 bar.

39. The process according to claim 17, wherein the pressure is between 2 and 5 bar.

40. The process according to claim 18, wherein the reaction temperature is between 273 K and 350 K.

41. The process according to claim 18, wherein the reaction temperature is between 274 K and 330.

42. The process according to claim 18, wherein the reaction temperature is between 295 and 310 K.

43. The process according to claim 19, wherein the quinolone is added at a ratio of the quinoline to and the Pd of between 2:1 and 150:1.

44. The process according to claim 19, wherein the quinolone is added at a ratio of the quinoline to and the Pd of between 5:1 and 50:1.

45. The process according to claim 19, wherein the quinolone is added at a ratio of the quinoline to and the Pd of between 10:1 and 30:1.

* * * * *